US012673960B2

(12) United States Patent
Mccall et al.

(10) Patent No.: US 12,673,960 B2
(45) Date of Patent: Jul. 7, 2026

(54) HETEROCYCLIC INHIBITORS OF Rho GTPases FOR THE TREATMENT OF DISEASE

(71) Applicant: MBQ Pharma, Canovanas, PR (US)

(72) Inventors: John Mccall, Boca Grande, FL (US); Eric Calderón-Ortiz, Cidra, PR (US)

(73) Assignee: MBQ Pharma, Canovanas, PR (US)

( * ) Notice: Subject to any disclaimer, the term of this patent is extended or adjusted under 35 U.S.C. 154(b) by 733 days.

(21) Appl. No.: 18/069,622

(22) Filed: Dec. 21, 2022

(65) Prior Publication Data

US 2023/0126139 A1 Apr. 27, 2023

Related U.S. Application Data

(63) Continuation of application No. PCT/US2021/040055, filed on Jul. 1, 2021.

(60) Provisional application No. 63/047,463, filed on Jul. 2, 2020.

(51) Int. Cl.

| | |
|---|---|
| ***C07D 519/00*** | (2006.01) |
| ***A61K 35/04*** | (2006.01) |
| ***A61K 45/06*** | (2006.01) |
| ***C07D 401/04*** | (2006.01) |
| ***C07D 403/04*** | (2006.01) |
| ***C07D 471/04*** | (2006.01) |
| ***C07D 487/04*** | (2006.01) |

(52) U.S. Cl.

CPC ............ *C07D 519/00* (2013.01); *A61K 35/04* (2013.01); *A61K 45/06* (2013.01); *C07D 401/04* (2013.01); *C07D 403/04* (2013.01); *C07D 471/04* (2013.01); *C07D 487/04* (2013.01)

(58) Field of Classification Search

None

See application file for complete search history.

(56) References Cited

U.S. PATENT DOCUMENTS

| | | | | |
|---|---|---|---|---|
| 4,835,258 | A | 5/1989 | Hollenberg | |
| 5,298,520 | A | 3/1994 | Baker | |
| 8,884,006 | B2 | 11/2014 | Hernandez | |
| 9,028,796 | B2 | 5/2015 | Maltese | |
| 9,169,234 | B2 | 10/2015 | Blagg | |
| 9,278,956 | B1 | 3/2016 | Hernandez | |
| 9,433,663 | B2 | 9/2016 | Zheng | |
| 9,616,064 | B2 | 4/2017 | Lawrence | |
| 9,981,980 | B2 | 5/2018 | Vlaar | |
| 12,209,078 | B2 * | 1/2025 | Jiménez | C07D 403/04 |
| 2009/0082340 | A1 | 3/2009 | Metz, Jr. | |
| 2010/0143474 | A1 | 6/2010 | Rommelspacher | |
| 2012/0022118 | A1 | 1/2012 | Demko | |
| 2017/0015635 | A1 | 1/2017 | Madadi | |
| 2023/0039997 | A1 | 2/2023 | Vlaar | |
| 2025/0230145 | A1 * | 7/2025 | Jiménez Cruz | C07D 403/04 |

FOREIGN PATENT DOCUMENTS

| | | | |
|---|---|---|---|
| CA | 2232260 | 4/1997 | |
| WO | 1997011695 | 4/1997 | |
| WO | 2004101767 | 11/2004 | |
| WO | 2007014198 | 2/2007 | |
| WO | WO-2017189893 A1 * | 11/2017 | A61K 31/403 |
| WO | 2022006377 | 1/2022 | |

OTHER PUBLICATIONS

Meyskens et. al. "Cancer Prevention: Obstacles, Challenges, and the Road Ahead" J Natl Cancer Inst 2016, 108, 2, djv309, 1-8. DOI: 10.1093/jnci/djv309. (Year: 2016).*

Cummings et. al. "Defining Disease Modifying Therapy for Alzheimer's Disease" The Journal of Prevention of Alzheimer's Disease 2017, 4, 2, 109-115. DOI: 10.14283/jpad.2017.12. (Year: 2017).*

Lin et. al. "Approaches of targeting Rho GTPases in cancer drug discovery" Expert Opin Drug Discov. 2015, 10, 9, 991-1010. DOI: 10.1517/17460441.2015.1058775. (Year: 2015).*

Aguilar et. al. "Rho GTPases as therapeutic targets in Alzheimer's disease" Alzheimer's Research & Therapy 2017, 9, 97, 1-10. DOI : 10.1186/s13195-017-0320-4. (Year: 2017).*

Cailleau et. al. "Long-term human breast carcinoma cell lines of metastatic origin: Preliminary characterization." In Vitro 1978, 14, 911-915. DOI: 10.1007/BF02616120. (Year: 1978).*

Humphries-Bickley et. al. "Characterization of a Dual Rac/Cdc42 Inhibitor MBQ-167 in Metastatic Cancer" Mol Cancer Ther 2017, 16, 5, 805-818. DOI: 10.1158/1535-7163.MCT-16-0442. Hereinafter Humphries. (Year: 2017).*

Perche et. al."Synthesis and formylation of 3-(2,5-dimethyl-1-pyrrolyl)-9-ethylcarbazole" Bulletin de la Societe Chimique de France 1974, 5-6, 1117-1118. ISSN: 0037-8968 (Year: 1974).*

International Application No. PCT/US2021/040055; International Preliminary Report on Patentability, date of issuance Jan. 12, 2023; 7 pages.

International Application No. PCT/US2021/040055; International Search Report and Written Opinion of the International Searching Authority, date of mailing Dec. 16, 2021; 10 pages.

Jiménez, J. et al., "Polymorphism in early development: The account of MBQ-167", Int J Pharm., 608:121064, 7 pages, (2021).

Jiménez, J. et al., "Solubility Measurements and Correlation of MBQ-167 in Neat and Binary Solvent Mixtures", J Chem Engin Data, 8 pages, (2020).

PubChem-SID: 386950363 Deposit Date: Nov. 4, 2019 (Apr. 11,2019) pp. 1-7: p. 2.

Castillo-Pichardo, L. et al., "The Rac Inhibitor EHop-016 Inhibits Mammary Tumor Growth and Metastasis in a Nude Mouse Model", Transl Oncol., 7(5): 546-55, (2014).

(Continued)

*Primary Examiner* — Jennifer A Berrios
*Assistant Examiner* — Sophia Reilly
(74) *Attorney, Agent, or Firm* — Global Patent Group Inc.; Cynthia Hathaway; Brock Levin

(57) ABSTRACT

The present invention relates to compounds and methods which may be useful as inhibitors of RhoGTPases for the treatment or prevention of cancer.

3 Claims, No Drawings

(56) References Cited

OTHER PUBLICATIONS

Dharmawardhane, S. et al., "Development of EHop-016: a small molecule inhibitor of Rac", Enzymes, 33 Pt A (Pt A): 117-46, (2013).
Golub, T. et al., "Molecular classification of cancer: class discovery and class prediction by gene expression monitoring", Science, 286(5439):531-7, (1999).
Hernández, E. et al., "Novel inhibitors of Rac1 in metastatic breast cancer", P R Health Sci J., 29(4):348-56, (2010).
Humphries-Bickley, T. et al., "Pharmacokinetics of Rac inhibitor EHop-016 in mice by ultra-performance liquid chromatography tandem mass spectrometry", J Chromatogr B Analyt Technol Biomed Life Sci., 981-2:19-26, (2015).
Lala, P. et al., "Role of nitric oxide in tumor progression: lessons from experimental tumors", Cancer Metastasis Rev., 17(1):91-106, (1998).
Lav, T. et al., "Elaboration and characterization of donor-acceptor polymer through electropolymerization of fullerene substituted N-alkylcarbazole", Synthetic metals, 162(21-22):1923-9, (2012).
Liu, Y. et al., "Biological evaluation of new mimetics of annonaceous acetogenins: alteration of right scaffold by click linkage with aromatic functionalities", Eur J Med Chem., 78:248-58, (2014).
Maldonado, M. et al., "Targeting Rae and Cdc42 GTPases in Cancer", Cancer Res., 78(12):3101-11, (2018).
Martin, H. et al., "Pak and Rac GTPases promote oncogenic KIT-induced neoplasms", J Clin Invest., 123(10): 4449-63, (2013).
Montalvo-Ortiz, B. et al., "Characterization of EHop-016, novel small molecule inhibitor of Rac GTPase", J Biol Chem., 287(16):13228-38, (2012).
PubChem: Substance Record for SID 239597128, (Feb. 13, 2015).
Rivera-Robles, M. et al., "Targeting Cdc42 with the anticancer compound MBQ-167 inhibits cell polarity and growth in the budding yeast *Saccharomyces cerevisiae*", Small GTPases, 11(6):430-40, (2020).
Surineni, G et al., "Rational design, synthesis and evaluation of novel-substituted 1, 2, 3-triazolylmethyl carbazoles as potent inhibitors of *Mycobacterium tuberculosis*", Med Chem Res., 24(3):1298-309, (2015).
Khoshkhoo, S. et al., "Crystallization of Polymorphs: The Effect I of Solvent", J Phys D Appl. Phys., 26:B90-3, (1993).
U.S. Appl. No. 17/938,091; Non-Final Office Action, dated Apr. 29, 2024; 15 pages.
U.S. Appl. No. 17/938,091; Notice of Allowance, dated Sep. 30, 2024; 13 pages.

* cited by examiner

HETEROCYCLIC INHIBITORS OF Rho GTPases FOR THE TREATMENT OF DISEASE

This application is a bypass continuation of International Application No. PCT/US2021/040055, filed Jul. 1, 2021, which claims the benefit of priority of U.S. Provisional Application No. 63/047,463, filed Jul. 2, 2020, the disclosures of each are hereby incorporated by reference as if written herein in their entireties.

BACKGROUND

Disclosed herein are heterocyclic compounds that inhibit Rho GTPases and are useful in their application as pharmaceuticals for the treatment of disease. Specifically, methods of inhibition of Rho ATPase activity in a human or animal subject are also provided for the treatment of diseases, including hyperproliferative and neoplastic diseases and cancer.

Novel compounds and pharmaceutical compositions, certain of which have been found to inhibit Rho GTPase activity have been discovered, together with methods of synthesizing and using the compounds including methods for the treatment of Rho GTPase-mediated diseases in a patient by administering the compounds. The Rho GTPases Rac (Ras-related C3 botulinum toxin substrate) and Cdc42 (cell division control protein 42 homolog) regulate cell functions governing cancer malignancy, including cell polarity, migration, and cell cycle progression. The Rho family of GTPases in humans consists of 20 different members, and aberrant behavior in their regulatory activity has been implicated in cancer and other diseases. More than 70 Guanine nucleotide Exchange Factors (GEFs) are known, which specifically activate one or more of the GTPases. In turn, the activated GTPases can specifically interact with over 60 downstream effectors. Dysregulation of one or more cellular processes can lead to release of malignant cells from their original locations, which subsequently can establish themselves in pre-metastatic niches in, for example, bone or lungs. It has been found that members of the Rho GTPase family, including Rac, Cdc42 and Rho, play key signaling roles in these processes.

Studies have implicated hyperactive Rac and Cdc42 with increased cancer cell survival, proliferation, and invasion, as well in Ras and other oncogene-mediated transformation. Furthermore, oncogenic cell surface receptors, such as tyrosine kinase, cytokine, and G protein coupled receptors, activate Rac and Cdc42 via regulation of their upstream effector GEFs. Accordingly, Rac and Cdc42 proteins are generally not mutated in cancer but rather overexpressed or hyperactivated. Even though ~9% of melanomas contain an activating Rac(P29S) mutation, and the hyperactive splice variant Racl bis overexpressed in some cancers, a majority of the Rac and Cdc42 in human cancer are activated due to upregulated GEFs.

Of the direct downstream effectors of Rac and Cdc42, p21-activated kinases (PAK) are overexpressed in a number of cancers and contribute to cancer transformation and progression by regulating key cellular functions, including cytoskeletal organization, cell migration, adhesion, growth, and development. Therefore, a number of PAK inhibitors have been developed as anti-cancer therapeutics. However, these have been limited by specificity, bioavailability and toxicity, and have yet to successfully complete clinical trials.

There is a need for new therapeutic agents for the treatment of cancer and other hyperproliferative diseases. The Rac and Cdc42 GTPases are important cellular mediators that are hyperactive or overexpressed in metastatic tumors. Design of novel inhibitors of the activities of Rac and/or Cdc42 with improved activity, pharmacochemical profile and reduced toxicity is desirable.

DETAILED DESCRIPTION

In certain embodiments of the present invention, compounds have structural Formula I:

(I)

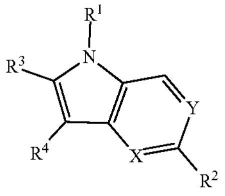

or a salt, ester, or prodrug thereof, wherein:

X and Y are independently chosen from CH and N $R^1$ is chosen from alkyl and cycloalkyl, either one of which is optionally substituted with one or more $R^5$;

$R^2$ is chosen from alkyl and cycloalkyl, either one of which is optionally substituted with one or more $R^6$;

$R^3$ and $R^4$ are independently chosen from H, alkyl, cycloalkyl, heterocycloalkyl, alkenyl, and alkynyl, any one of which is optionally substituted with one or more $R^7$, or $R^3$ and $R^4$, together with the intervening atoms, combine to form a 5- to 7-membered aryl or heteroaryl, either one of which is optionally substituted with one or more $R^7$;

each $R^5$, $R^6$, and $R^7$ is independently chosen from cyano, halo, hydroxy, oxo, alkyl, cycloalkyl, heterocycloalkyl, aryl, and heteroaryl.

In certain embodiments, $R^3$ and $R^4$ are independently chosen from H, alkyl, cycloalkyl, heterocycloalkyl, alkenyl, and alkynyl, any one of which is optionally substituted with one or more $R^7$.

In certain further embodiments, $R^3$ is chosen from alkyl, cycloalkyl, and heterocycloalkyl, any one of which is optionally substituted with one or more $R^7$. In certain further embodiments, $R^3$ is chosen from alkyl and cycloalkyl, either one of which is optionally substituted with one or more $R^7$. In certain further embodiments, $R^3$ is cycloalkyl, which is optionally substituted with one or more $R^7$. In certain further embodiments, $R^3$ is bicyclo[1.1.1]pentan-2-yl, which is optionally substituted with one or more $R^7$. In certain further embodiments, $R^3$ is

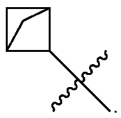 [SMILES: *C1C2CC1C2]

In certain embodiments, $R^4$ is chosen from H, alkyl, cycloalkyl, and heterocycloalkyl, any one of which is optionally substituted with one or more $R^7$. In certain further embodiments, $R^4$ is H or is chosen from alkyl and cycloalkyl, either one of which is optionally substituted with one or more $R^7$. In certain further embodiments, $R^4$ is H.

In certain embodiments, $R^3$ and $R^4$, together with the intervening atoms, combine to form a 5- to 7-membered aryl or heteroaryl, either one of which is optionally substituted with one or more $R^7$.

In certain embodiments, $R^3$ and $R^4$, together with the intervening atoms, combine to form a 6-membered aryl or heteroaryl, either one of which is optionally substituted with one or more $R^7$.

In certain embodiments, $R^3$ and $R^4$, together with the intervening atoms, combine to form phenyl or pyridyl, either one of which is optionally substituted with one or more $R^7$.

In certain embodiments, the compounds have structural Formula Ia:

(Ia)

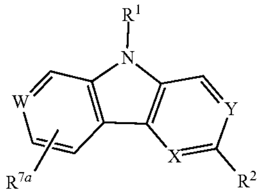

or a salt, ester, or prodrug thereof, wherein:

W is chosen from CH and N;

X and Y are independently chosen from CH and N;

W and the intervening atoms combine to form a six-membered aryl or six-membered heteroaryl substituted by $R^{7a}$;

$R^1$ is chosen from alkyl and cycloalkyl, either one of which is optionally substituted with one or more $R^5$;

$R^2$ is chosen from alkyl and cycloalkyl, either one of which is optionally substituted with one or more $R^6$;

each $R^5$ and $R^6$ is independently chosen from cyano, halo, hydroxy, oxo, alkyl, cycloalkyl, heterocycloalkyl, aryl, and heteroaryl; and $R^{7a}$ is chosen from H, cyano, halo, hydroxy, oxo, alkyl, cycloalkyl, heterocycloalkyl, aryl, and heteroaryl.

In certain embodiments, W is CH.

In certain embodiments, W is N.

In certain embodiments, $R^2$ is chosen from

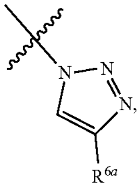, 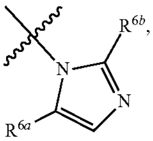, 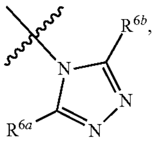, 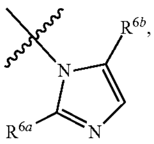, 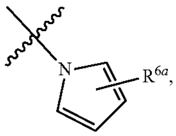, 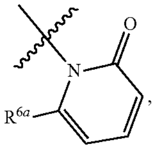,

-continued

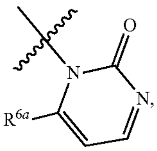, 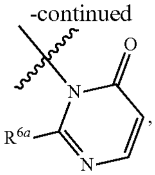, 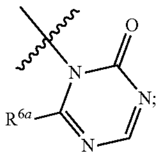;

and $R^{6a}$ is chosen from H, cyano, halo, hydroxy, alkyl, cycloalkyl, heterocycloalkyl, aryl, and heteroaryl.

In certain embodiments, $R^2$ is chosen from

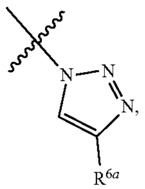, 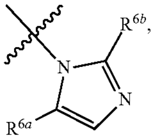, 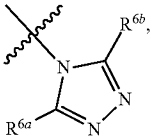, 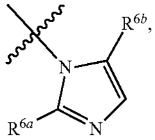, and 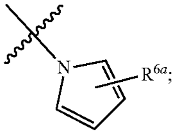;

and $R^{6a}$ is chosen from H, cyano, halo, hydroxy, alkyl, cycloalkyl, heterocycloalkyl, aryl, and heteroaryl.

In certain embodiments, $R^2$ is chosen from

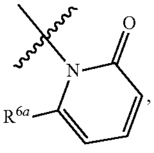, 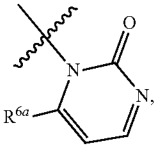, 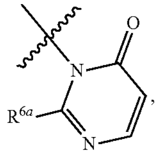, 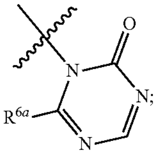;

and $R^{6a}$ is chosen from H, cyano, halo, hydroxy, alkyl, cycloalkyl, heterocycloalkyl, aryl, and heteroaryl.

In certain embodiments, $R^2$ is chosen from

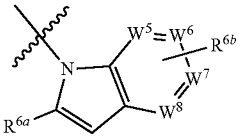 and 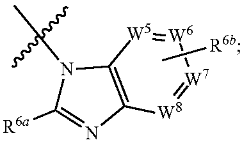;

$W^5$, $W^6$, $W^7$, and $W^8$ are independently chosen from CH and N;

$W^5$, $W^6$, $W^7$, and $W^8$ and the intervening atoms combine to form a six-membered aryl or six-membered heteroaryl substituted by $R^{6b}$; and $R^{6a}$ and $R^{6b}$ are independently chosen from H, cyano, halo, hydroxy, oxo, alkyl, cycloalkyl, heterocycloalkyl, aryl, and heteroaryl.

Certain compounds disclosed herein may possess useful Rho GTPase inhibiting activity, and may be used in the treatment or prophylaxis of a disease or condition in which Rho GTPase plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting Rho GTPase. Other embodiments provide methods for treating a Rho GTPase-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of Rho GTPase.

Compounds disclosed herein may be substituted with compounds of Formula I or compounds of any of Formula I, Ia, IIa, IIb, IIc, III, and IIIa.

In certain embodiments, the compounds have structural Formula Ia:

(Ia)

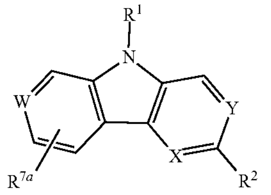

or a salt, ester, or prodrug thereof, wherein:

W is chosen from CH and N;

X and Y are independently chosen from CH and N;

W and the intervening atoms combine to form a six-membered aryl or six-membered heteroaryl substituted by $R^{7a}$;

$R^1$ is chosen from alkyl and cycloalkyl, either one of which is optionally substituted with one or more $R^5$;

$R^2$ is chosen from alkyl and cycloalkyl, either one of which is optionally substituted with one or more $R^6$;

each $R^5$ and $R^6$ is independently chosen from cyano, halo, hydroxy, oxo, alkyl, cycloalkyl, heterocycloalkyl, aryl, and heteroaryl; and $R^{7a}$ is chosen from H, cyano, halo, hydroxy, oxo, alkyl, cycloalkyl, heterocycloalkyl, aryl, and heteroaryl.

In certain embodiments, W is CH.

In certain embodiments, W is N.

In certain embodiments, $R^2$ is chosen from

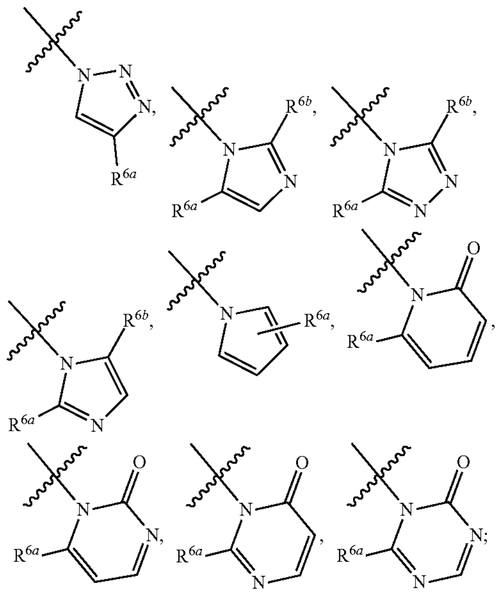

and $R^{6a}$ is chosen from H, cyano, halo, hydroxy, alkyl, cycloalkyl, heterocycloalkyl, aryl, and heteroaryl.

In certain embodiments, $R^2$ is chosen from

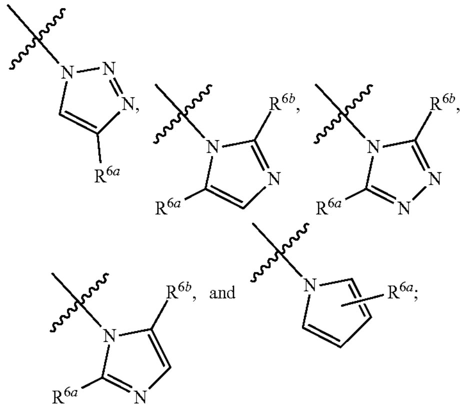

and $R^{6a}$ is chosen from H, cyano, halo, hydroxy, alkyl, cycloalkyl, heterocycloalkyl, aryl, and heteroaryl.

In certain embodiments, $R^2$ is chosen from

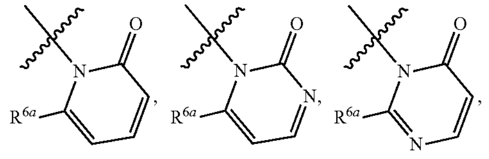

-continued

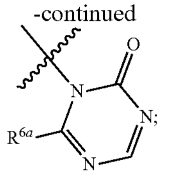

and $R^{6a}$ is chosen from H, cyano, halo, hydroxy, alkyl, cycloalkyl, heterocycloalkyl, aryl, and heteroaryl.

In certain embodiments, $R^2$ is chosen from

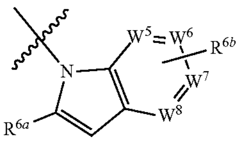

and

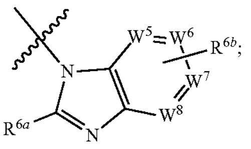

$W^5$, $W^6$, $W^7$, and $W^8$ are independently chosen from CH and N;

$W^5$, $W^6$, $W^7$, and $W^8$ and the intervening atoms combine to form a six-membered aryl or six-membered heteroaryl substituted by $R^{6b}$; and $R^{6a}$ and $R^{6b}$ are independently chosen from H, cyano, halo, hydroxy, oxo, alkyl, cycloalkyl, heterocycloalkyl, aryl, and heteroaryl.

In certain embodiments, the compounds have structural Formula II:

(II)

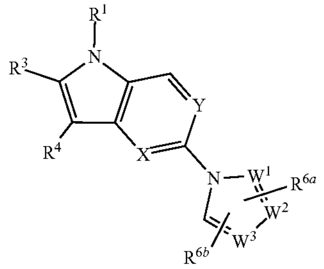

or a salt, ester, or prodrug thereof, wherein:

$W^1$, $W^2$, and $W^3$ are independently chosen from CH and N;

$W^1$, $W^2$, and $W^3$ and the intervening atoms combine to form a five-membered heteroaryl substituted by $R^{6a}$ and $R^{6b}$;

X and Y are independently chosen from CH and N $R^1$ is chosen from alkyl and cycloalkyl, either one of which is optionally substituted with one or more $R^5$;

$R^3$ and $R^4$ are independently chosen from H, alkyl, cycloalkyl, heterocycloalkyl, alkenyl, and alkynyl, any one of which is optionally substituted with one or more $R^7$, or $R^3$ and $R^4$, together with the intervening atoms, combine to form a 5- to 7-membered aryl or heteroaryl, either one of which is optionally substituted with one or more $R^7$;

$R^{6a}$ and $R^{6b}$ are independently chosen from H, cyano, halo, hydroxy, oxo, alkyl, cycloalkyl, heterocycloalkyl, aryl, and heteroaryl, or $R^{6a}$ and $R^{6b}$, together with the intervening atoms, combine to form a 5- or 6-membered heterocycloalkyl or a 5- or 6-membered heteroaryl; and each $R^5$ and $R^7$ is independently chosen from cyano, halo, hydroxy, alkyl, cycloalkyl, heterocycloalkyl, aryl, and heteroaryl.

In certain embodiments, the compounds have structural Formula IIa:

(IIa)

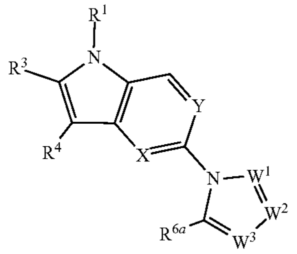

or a salt, ester, or prodrug thereof, wherein:

$W^1$, $W^2$, and $W^3$ are independently chosen from CH and N;

$W^1$, $W^2$, and $W^3$ and the intervening atoms combine to form a five-membered heteroaryl substituted by $R^{6a}$ and $R^{6b}$;

X and Y are independently chosen from CH and N $R^1$ is chosen from alkyl and cycloalkyl, either one of which is optionally substituted with one or more $R^5$;

$R^3$ and $R^4$ are independently chosen from H, alkyl, cycloalkyl, heterocycloalkyl, alkenyl, and alkynyl, any one of which is optionally substituted with one or more $R^7$, or $R^3$ and $R^4$, together with the intervening atoms, combine to form a 5- to 7-membered aryl or heteroaryl, either one of which is optionally substituted with one or more $R^7$;

$R^{6a}$ is chosen from H, cyano, halo, hydroxy, oxo, alkyl, cycloalkyl, heterocycloalkyl, aryl, and heteroaryl; and each $R^5$ and $R^7$ is independently chosen from cyano, halo, hydroxy, alkyl, cycloalkyl, heterocycloalkyl, aryl, and heteroaryl.

In certain embodiments, $R^{6a}$ and $R^{6b}$ are independently chosen from H, cyano, halo, hydroxy, oxo, alkyl, cycloalkyl, heterocycloalkyl, aryl, and heteroaryl.

In certain embodiments, $R^{6a}$ and $R^{6b}$, together with the intervening atoms, combine to form a 5- or 6-membered heterocycloalkyl or a 5- or 6-membered heteroaryl.

In certain embodiments, 0, 1, 2, or 3 of $W^1$, $W^2$, and $W^3$ are N.

In certain embodiments, 0, 1, or 2, of $W^1$, $W^2$, and $W^3$ are N.

In certain embodiments, 0 or 1 of $W^1$, $W^2$, and $W^3$ is N.

In certain embodiments, 1 of $W^1$, $W^2$, and $W^3$ is N.

In certain embodiments, 2 of $W^1$, $W^2$, and $W^3$ are N.

In certain embodiments, the compounds have structural Formula IIb:

(IIb)

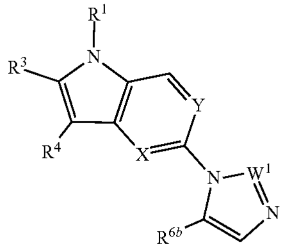

or a salt, ester, or prodrug thereof, wherein:

$W^1$ is chosen from $C(R^{6a})$ and N;

X and Y are independently chosen from CH and N $R^1$ is chosen from alkyl and cycloalkyl, either one of which is optionally substituted with one or more $R^5$;

$R^3$ and $R^4$ are independently chosen from H, alkyl, cycloalkyl, heterocycloalkyl, alkenyl, and alkynyl, any one of which is optionally substituted with one or more $R^7$, or $R^3$ and $R^4$, together with the intervening atoms, combine to form a 5- to 7-membered aryl or heteroaryl, either one of which is optionally substituted with one or more $R^7$;

$R^{6a}$ and $R^{6b}$ are independently chosen from H, cyano, halo, hydroxy, oxo, alkyl, cycloalkyl, heterocycloalkyl, aryl, and heteroaryl; and each $R^5$ and $R^7$ is independently chosen from cyano, halo, hydroxy, alkyl, cycloalkyl, heterocycloalkyl, aryl, and heteroaryl.

In certain embodiments, $W^1$ is $C(R^{6a})$.

In certain embodiments, $W^1$ is N.

In certain embodiments, the compounds have structural Formula IIc:

(IIc)

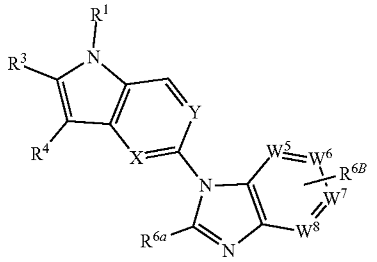

or a salt, ester, or prodrug thereof, wherein:

$W^5$, $W^6$, $W^7$, and $W^8$ are independently chosen from CH and N;

$W^5$, $W^6$, $W^7$, and $W^8$ and the intervening atoms combine to form a six-membered aryl or six-membered heteroaryl substituted by $R^{6b}$;

X and Y are independently chosen from CH and N $R^1$ is chosen from alkyl and cycloalkyl, either one of which is optionally substituted with one or more $R^5$;

$R^3$ and $R^4$ are independently chosen from H, alkyl, cycloalkyl, heterocycloalkyl, alkenyl, and alkynyl, any one of which is optionally substituted with one or more $R^7$, or $R^3$ and $R^4$, together with the intervening atoms, combine to form a 5- to 7-membered aryl or heteroaryl, either one of which is optionally substituted with one or more $R^7$;

$R^{6a}$ and $R^{6b}$ are independently chosen from H, cyano, halo, hydroxy, oxo, alkyl, cycloalkyl, heterocycloalkyl, aryl, and heteroaryl; and each $R^5$ and $R^7$ is independently chosen from cyano, halo, hydroxy, alkyl, cycloalkyl, heterocycloalkyl, aryl, and heteroaryl.

In certain embodiments, 0, 1, or 2 of $W^5$, $W^6$, $W^7$, and $W^8$ are N.

In certain embodiments, 0 or 1 of $W^5$, $W^6$, $W^7$, and $W^8$ are N.

In certain embodiments, 1 of $W^5$, $W^6$, $W^7$, and $W^8$ is N.

In certain embodiments, the compounds have structural Formula III:

(III)

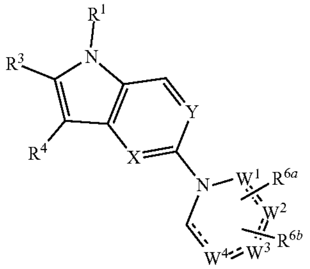

or a salt, ester, or prodrug thereof, wherein:

$W^1$, $W^2$, $W^3$, and $W^4$ are independently chosen from CH and N;

$W^1$, $W^2$, $W^3$, and $W^4$ and the intervening atoms combine to form a six-membered heterocycloalkyl or heteroaryl, either one of which is substituted by $R^{6a}$ and $R^{6b}$;

X and Y are independently chosen from CH and N $R^1$ is chosen from alkyl and cycloalkyl, either one of which is optionally substituted with one or more $R^5$;

$R^3$ and $R^4$ are independently chosen from H, alkyl, cycloalkyl, heterocycloalkyl, alkenyl, and alkynyl, any one of which is optionally substituted with one or more $R^7$, or $R^3$ and $R^4$, together with the intervening atoms, combine to form a 5- to 7-membered aryl or heteroaryl, either one of which is optionally substituted with one or more $R^7$;

$R^{6a}$ and $R^{6b}$ are independently chosen from H, cyano, halo, hydroxy, oxo, alkyl, cycloalkyl, heterocycloalkyl, aryl, and heteroaryl, or $R^{6a}$ and $R^{6b}$, together with the intervening atoms, combine to form a 5- or 6-membered heterocycloalkyl or a 5- or 6-membered heteroaryl; and each $R^5$ and $R^7$ is independently chosen from cyano, halo, hydroxy, alkyl, cycloalkyl, heterocycloalkyl, aryl, and heteroaryl.

In certain embodiments, the compounds have structural Formula IIIa:

(IIIa)

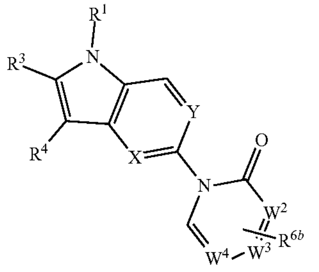

or a salt, ester, or prodrug thereof, wherein:

$W^2$, $W^3$, and $W^4$ are independently chosen from CH and N;

$W^2$, $W^3$, and $W^4$ and the intervening atoms combine to form a six-membered heterocycloalkyl, either one of which is substituted by $R^{6a}$ and $R^{6b}$;

X and Y are independently chosen from CH and N $R^1$ is chosen from alkyl and cycloalkyl, either one of which is optionally substituted with one or more $R^5$;

$R^3$ and $R^4$ are independently chosen from H, alkyl, cycloalkyl, heterocycloalkyl, alkenyl, and alkynyl, any one of which is optionally substituted with one or more $R^7$, or $R^3$ and $R^4$, together with the intervening atoms, combine to form a 5- to 7-membered aryl or heteroaryl, either one of which is optionally substituted with one or more $R^7$;

$R^{6b}$ is chosen from H, cyano, halo, hydroxy, oxo, alkyl, cycloalkyl, heterocycloalkyl, aryl, and heteroaryl; and each $R^5$ and $R^7$ is independently chosen from cyano, halo, hydroxy, alkyl, cycloalkyl, heterocycloalkyl, aryl, and heteroaryl.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present invention also relates to a method of inhibiting at least one Rho GTPase function comprising the step of contacting Rho GTPase with a compound as described herein. The cell phenotype, cell proliferation, activity of Rho GTPase, change in biochemical output produced by active Rho GTPase, expression of Rho GTPase, or binding of Rho GTPase with a natural binding partner may be monitored. Such methods may be modes of treatment of disease, biological assays, cellular assays, biochemical assays, or the like.

Also provided herein is a method of treatment of a Rho GTPase-mediated disease comprising the administration of a therapeutically effective amount of a compound as disclosed herein, or a salt thereof, to a patient in need thereof.

In certain embodiments, the Rho GTPase-mediated disease is chosen from cancer.

Also provided herein is a compound as disclosed herein for use as a medicament.

Also provided herein is a compound as disclosed herein for use as a medicament for the treatment of a Rho GTPase-mediated disease.

Also provided is the use of a compound as disclosed herein as a medicament.

Also provided is the use of a compound as disclosed herein as a medicament for the treatment of a Rho GTPase-mediated disease.

Also provided is a compound as disclosed herein for use in the manufacture of a medicament for the treatment of a Rho GTPase-mediated disease.

Also provided is the use of a compound as disclosed herein for the treatment of a Rho GTPase-mediated disease.

Also provided herein is a method of inhibition of Rho GTPase comprising contacting Rho GTPase with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the Rho GTPase-mediated disease is chosen from cancer.

Also provided is a method of modulation of a Rho GTPase-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a $-C(O)CH_3$ group. An "alkylcarbonyl" or "alkanoyl" group refers to an alkyl group attached to the parent molecular moiety through a carbonyl group.

Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene ($—CH_2—$). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl,"as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH—$).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl,"as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group- with R and R' as defined herein.

The term "N-carbamyl" as used herein, alone or in combination, refers to a ROC(0)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS-group, where R is as defined herein.

The term "nitro," as used herein, alone or in combination, refers to —$NO_2$.

The terms "oxy" or "oxa," as used herein, alone or in combination, refer to —O.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a $RS(=O)_2NR'$-group with R and R' as defined herein.

The term "S-sulfonamido" refers to a —$S(=O)_2NRR'$, group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R'as defined herein.

The term "O-thiocarbamyr" refers to a —OC(S)NRR', group with R and R' as defined herein.

The term "thiocyanato" refers to a —CNS group.

The term "trihalomethanesulfonamido" refers to a $X_3CS(O)_2NR$— group with X is a halogen and R as defined herein.

The term "trihalomethanesulfonyl" refers to a $X_3CS(O)_2$— group where X is a halogen.

The term "trihalomethoxy" refers to a $X_3CO$— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and $R^n$ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammal1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating Rho GTPase-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of Rho GTPase-mediated disorders.

Specific diseases to be treated by the compounds, compositions, and methods disclosed herein include neoplasm, malignant; carcinoma; carcinoma, undifferentiated; giant and spindle cell carcinoma; small cell carcinoma; small cell lung cancer; non-small cell lung cancer; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

General Synthetic Methods for Preparing Compounds

The following schemes can be used to practice the present invention.

Scheme I

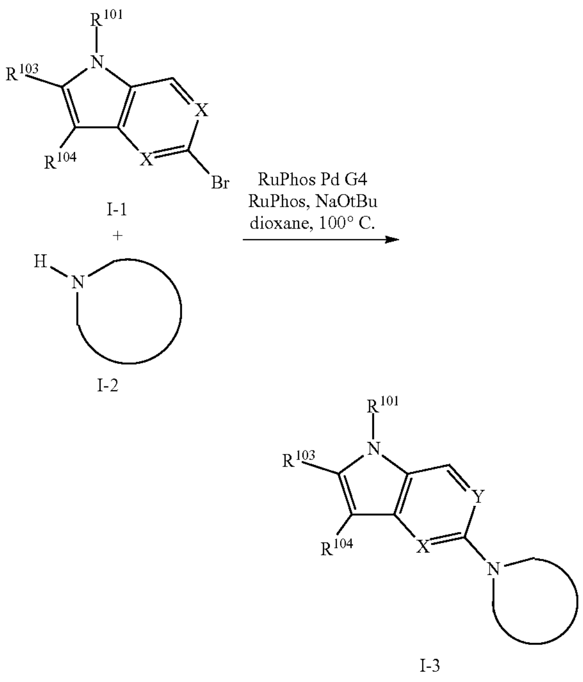

Certain compounds of the present disclosure can be synthesized using the general synthetic procedure set forth in Scheme I. A suitably derivatized bromo indole I-1 is reacted with a heterocyclic or heteroaromatic amine, represented by I-2, under Buchwald coupling conditions to give product I-3. Further synthetic modifications, including deprotection and functional group transformations, can be performed in following steps (not shown).

Scheme II

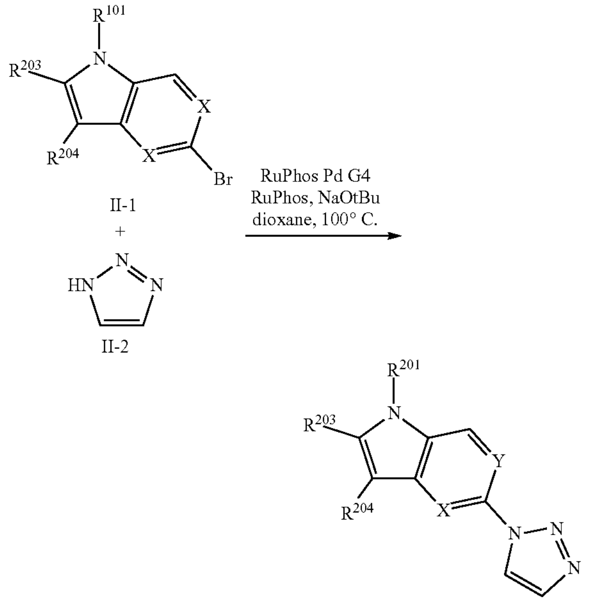

II-1 + II-2 → II-3

Certain compounds of the present disclosure can be synthesized using the general synthetic procedure set forth in Scheme II. A suitably derivatized bromo indole II-1 is reacted with a heteroaromatic amine, such as 1,2,3-triazole II-2, under Buchwald coupling conditions to give product II-3. Further synthetic modifications, including deprotection and functional group transformations, can be performed in following steps (not shown).

Scheme III

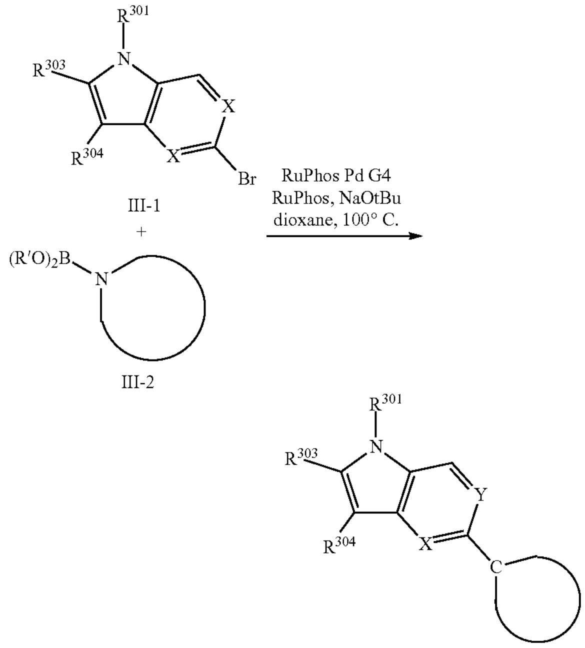

III-1 + III-2 → III-3

Certain compounds of the present disclosure can be synthesized using the general synthetic procedure set forth in Scheme III. A suitably derivatized bromo indole III-1 is reacted with an aromatic or heteroaromatic boronic acid (R'═H) or boronic ester (R'=alkyl), represented by III-2, under Suzuki coupling conditions to give product III-3. Further synthetic modifications, including deprotection and functional group transformations, can be performed in following steps (not shown).

The activity of the compounds as disclosed herein as Rho GTPase can be illustrated in the following assay(s). The other compounds listed above, which have not yet been made and/or tested, are predicted to have activity in these assay(s) as well.

Biological Activity Assay

Rac and Cdc42 Activation Assays

For the $IC_{50}$ curves: Rac 1/2/3 and Cdc42 activation is determined as described, using a G-LISA kit (Cytoskeleton, Inc., Denver, Colo.). MDA-MB-231 cell lysates are prepared from 24 h treatment with compounds as disclosed herein by combining attached and detached cell populations (N=3). Four-parameter dose-response IC50 curves are fitted using the nonlinear regression function of GraphPad Prism®.

Additionally, Rac, Cdc42, or Rac activation is determined, by pulldowns using the P21-binding domain (PBD) of PAK, or Rho binding domain of Rhotekin as described (2, 16). The GTP bound active Rac, Cdc42, or Rho is detected by Western blot (N=3).

Western Blot Analysis

Total cell lysates or pull-downs are Western blotted using routine procedures. The primary antibodies used are: Rac (Rac1,2,3), Cdc42, Bcl-xL, Bcl-2, Mcl-1, PAK1, PAK2, phospho (p)-PAK1(T423)/PAK2(T402), p-PAK1(S199/204)/PAK2(S192/197), p-PAK1(S144/204)/PAK2(S141), LIM kinase (LIMK1), p-LIMK1/2(Tyr507/Thr508), Cofilin, p-cofilin(S3), STAT3, p-STAT3(Y705), p-P-38 MAPK (T180/Y182), p-ERK (T202/Y204), p-Akt (S473), and Akt (Cell Signaling Technology, Inc.) and (β-actin (Sigma).

Fluorescence Microscopy

MDA-MB-231 cells are treated with vehicle or a compound as disclosed herein at 250 or 500 nM for 24 h. Cells are fixed, permeabilized, and stained with Rhodamine phalloidin to visualize F-actin, and with p-tyrosine or vinculin to visualize focal adhesions, as described (2). Fluorescence micrographs are acquired at 600× in an Olympus BX40 fluorescence microscope using a Spot digital camera.

Cell Migration Assays

Transwell Assay

As described, quiescent MDA-MB-231 cells are treated with vehicle or any one of the compounds disclosed herein (250 nM) for 24 h. The attached and detached populations are separated and $2\times10^5$ cells were placed on the top well of Transwell chambers with 5% FBS in the bottom well. The number of cells that migrated to the underside of the membrane following a 7 h incubation is quantified after staining fixed cells with propidium iodide (PI). For each treatment (N=3), cells in 20 microscopic fields are quantified.

Wound Healing Scratch Assay

MDA-MB-231 cells plated on 6-well plates at equal cell density are incubated in 10% FBS until confluent. The media is changed to 2% FBS and a single scratch is made in the center of the monolayer culture with a pipet tip. Any one of the compounds as described herein was added at 0, 250, or 500 nM immediately following wounding. Images are digitally acquired from an Olympus microscope (4× magnification) at 0, 8, 12, and 24 h and the scratch distance quantified in Adobe Photoshop. N=3 biological replicates (with 2 technical replicates each).

Mammosphere Formation Assay

As described, equal numbers of MDA-MB-231 cells treated with vehicle or any one of the compounds described herein are seeded in ultra-low attachment plates (Corning) at a density of 500 cells/well in serum-free mammary epithelium basal medium (Lonza). Mammospheres are counted after 4 days incubation in 0 or 250 nM of a compound as disclosed herein at 37° C., 5% $CO_2$. Mammosphere-forming efficiency is calculated as the number of mammospheres divided by the number of cells seeded per well and expressed relative to vehicle controls.

Cell Viability Assays

As described, equal numbers of MDA-MB-231, GFP-HER2-BM, or MCF-10A cells are incubated in 0-1 μM or any one of the compounds described herein for 120 h. The CellTiter 96® Non-Radioactive Cell Proliferation Assay (Promega, Fitchburg, Wis.) was used according to the manufacturer's instructions. This assay allows the quantification of the viability of both attached and detached cells in the same well. GI50 was determined as 100×(T−T0)/(C−T0)=50 (T=the optical density of drug treatment after 120 h, T0=the optical density at time zero, and C=the optical density of the untreated cells). Curves are fitted using the four-parameter logistic nonlinear regression models in GraphPad Prism software.

Cell Cycle Progression

MDA-MB-231 cells are incubated with 0 or 250 nM of a compound as disclosed herein for 48 h and all cells (detached and attached) are stained with PI, as in (27). Cell cycle stage is analyzed using a four-color flow cytometer (FACSCalibur, BD Biosciences, San Jose, Calif.). A total of 20,000 events are analyzed for each sample. List-mode files are collected using Cell Quest software 3.3 and analyzed using the Flow Jo software vX.0.7 (BD Biosciences, San Jose, Calif.).

Apoptosis Assay

Apoptosis is measured using a Caspase-Glo3/7 Luminescence Assay Kit as per manufacturer's instructions (Promega, Corp., Madison, WI, USA). Following treatment of equal numbers of cells with vehicle or for 24 h, Caspase-3/7 Glo reagent is added and incubated at room temperature for 60 min. Caspase-3/7 activities are determined by quantifying luminescence.

Annexin V Staining

Apoptotic cells are detected by fluorescence microscopy of Annexin V-Cy3-18 stained cells as per manufacturer's instructions (Sigma-Aldrich, St. Louis, MO, USA). Briefly, GFP-MDA-MB-231 cells grown on coverslips are treated with vehicle, or 250 or 500 nM of a compound as disclosed herein for 6 h and stained with Annexin V-Cy3-18 in binding buffer (10 mM HEPES/NaOH, pH 7.5, 0.14 M NaCl, 2.5 mM CaCl2) for 15 min at room temperature. Coverslips are washed in binding buffer and fixed with 3.7% paraformaldehyde prior to fluorescence microscopy. Images are digitally acquired from an Olympus inverted fluorescence microscope.

Animal Protocol

All animal studies are conducted in accordance with the NIH Guideline for the Care and Use of Laboratory Animals. Female athymic nu/nu mice and severe combined immunodeficiency Crl:SHO-Prkdc SCID Hairless 4 to 5 wk old (Charles River Laboratories, Inc., Wilmington, Mass.) are maintained under pathogen-free conditions in HEPA-filtered cages.

Tumor Establishment

GFP-HER2-BM cells (~5×105) or GFP-MDA-MB-231 cells (1×105) in Matrigel (BD Biosciences, San Jose, Calif.) are injected at the fourth right mammary fat pad under isofluorane inhalation (1-3% in oxygen using an inhalation chamber at 2 L/min) to produce orthotopic primary tumors. After tumor establishment (1 wk post-inoculation), animals are randomly divided into treatment groups (n=6).

Administration of a Compound as Disclosed Herein

Mice are treated with vehicle (12.5% ethanol, 12.5% Cremophor (Sigma-Aldrich, St. Louis, Mo.), and 75% 1×PBS pH 7.4), or 1 or 10 mg/kg BW of a compound as disclosed herein by i.p. injection in a 100 μL volume 3× a wk. Treatments continued until sacrifice at day 65.

Whole Body Fluorescence Image Analysis

Mammary tumor growth is quantified as changes in the integrated density of GFP fluorescence. Mice are imaged on day 1 of treatment administration, and once a week thereafter for 65 days, using the FluorVivo small animal in vivo imaging system (INDEC Systems, Inc., Santa Clara, Calif.). Tumor fluorescence intensities are analyzed using Image J software (National Institutes of Health, Bethesda, Md.). Relative tumor growth is calculated as the integrated density of fluorescence of each tumor on each day of imaging relative to the integrated density of fluorescence of the same tumor on day 1 of treatment. Optimal tumor growth is calculated as % T/C=(δT/δC)×100 when δT>0, δT=average tumor size on day 65 of treated mice-average tumor size on day 01 of treated mice. δC=average tumor size on day 65 of control mice-average tumor size on day 01 of control mice. Tumor growth delay is calculated as the percentage by which the treated group tumor size is delayed in attaining a specified number of doublings (from day 1) compared with controls using: [(T−C)/C]×100, where T and C are the median times in days for treated and control groups to double in tumor size.

Analysis of Metastases

Following sacrifice, lungs, kidneys, livers, bones, and spleens are excised and immediately stored in liquid $N_2$. Stored organs are thawed and analyzed by fluorescence microscopy, as described.

Liver Enzyme Assays

Frozen stored livers are thawed and homogenized to measure alkaline phosphatase (ALP) and alanine transaminase (ALT) activities using colorimetric assay kits from Abcam and Cayman Chemicals respectively, as per manufacturer's instructions.

Statistical Analysis

Statistical analyses use Microsoft Excel and GraphPad Prism, and differences are considered statistically significant at P≤0.05.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising a compound of structural Formula II:

(II)

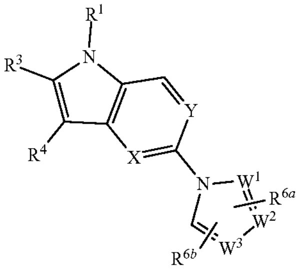

or a salt, ester, or prodrug thereof, wherein:

$W^1$, $W^2$, and $W^3$ are independently chosen from CH and N;

$W^1$, $W^2$, and $W^3$ and the intervening atoms combine to form a five-membered heteroaryl substituted by $R^{6b}$ and $R^{6b}$;

X and Y are independently chosen from CH and N $R^1$ is chosen from alkyl and cycloalkyl, either one of which is optionally substituted with one or more $R^5$;

$R^3$ and $R^4$ are independently chosen from H, alkyl, cycloalkyl, heterocycloalkyl, alkenyl, and alkynyl, any one of which is optionally substituted with one or more $R^7$, or $R^3$ and $R^4$, together with the intervening atoms, combine to form a 5-to 7-membered aryl or heteroaryl, either one of which is optionally substituted with one or more $R^7$;

$R^{6a}$ and $R^{6b}$ are independently chosen from from cyano, halo, hydroxy, oxo, alkyl, cycloalkyl, heterocycloalkyl, aryl, and heteroaryl, or $R^{6b}$ and $R^{6b}$, together with the intervening atoms, combine to form a 5-or 6-membered heterocycloalkyl or a 5-or 6-membered heteroaryl; and each $R^5$ and $R^7$ is independently chosen from from cyano, halo, hydroxy, alkyl, cycloalkyl, heterocycloalkyl, aryl, and heteroaryl, together with a pharmaceutically acceptable carrier.

2. A method of inhibition of Rho GTPase comprising contacting Rho GTPase with a pharmaceutical composition as recited in claim 1.

3. A method of treating a Rho GTPase-mediated disease comprising administering a therapeutically effective amount of a pharmaceutical composition as recited in claim 1 to a patient in need thereof wherein the disease is chosen from oral squamous cell carcinoma, gastric cell carcinoma, breast cancer, lung cancer, testicular cancer, prostate cancer, colorectal cancer, melanoma, non-small cell lung cancer, or head and neck squamous cell carcinoma.

* * * * *